United States Patent [19]

Parker et al.

[11] Patent Number: 4,717,760
[45] Date of Patent: Jan. 5, 1988

[54] FLUORINATED TRIS-EPOXIDES BASED ON TRIPHENYL METHANE

[75] Inventors: Theodore L. Parker, Lafayette; Robert R. Stringham, Concord, both of Calif.

[73] Assignee: The Dow Chemical Company, Midland, Mich.

[21] Appl. No.: 884,144

[22] Filed: Jul. 10, 1986

[51] Int. Cl.$^4$ .................. C08G 59/32; C07D 303/02; C07D 303/08
[52] U.S. Cl. ........................ 528/98; 528/102; 549/523; 549/550; 549/559
[58] Field of Search ............. 528/98, 102; 549/523, 549/550, 559, 563

[56] References Cited

U.S. PATENT DOCUMENTS

| | | | |
|---|---|---|---|
| 3,706,772 | 12/1972 | Reines | 549/559 |
| 3,879,430 | 4/1975 | O'Rear et al. | 528/402 X |
| 4,394,496 | 7/1983 | Schrader | 528/98 |

*Primary Examiner*—Earl Nielsen
*Attorney, Agent, or Firm*—Norman L. Sims

[57] ABSTRACT

Epoxides of the invention are those of the formula

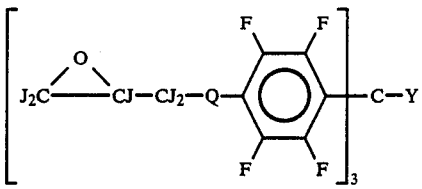

wherein J is H or F, the same in each occurrence; Q is a valence bond or —O—, the same in each occurrence; and Y is H or F, independently. When cured, these epoxides are superior in moisture resistance, flame retardance, and thermal stability to the corresponding non-fluorinated, prior art epoxides. The epoxides of the preceding formula may be made by first reacting an allylic halide of the formula $CJ_2=CJ-CJ_2-X$, wherein X is halogen, with a compound of the formula

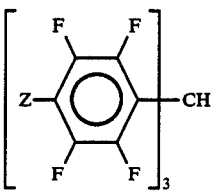

wherein Z is MO, hal.Mg or Ag; M is an alkali metal; and hal=Br or I; then if Y is to be F, converting the —CH group to a —CF group, and finally, oxidizing the $CJ_2=CJ$ group to a

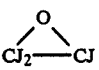

group.

17 Claims, No Drawings

FLUORINATED TRIS-EPOXIDES BASED ON TRIPHENYL METHANE

FIELD OF THE INVENTION

The present invention relates to triphenyl-methane-based tri-epoxides and polyhalogenated aromatic epoxides.

BACKGROUND OF THE INVENTION

U.S. Pat. No. 4,394,496 discloses triglycidyl ethers of 1,1,1-tri(hydroxyphenyl) alkanes and oligomeric reaction products of the ethers with the triphenols. These epoxides have superior high temperature properties, excellent mechanical properties, and good moisture resistance. They are of considerable interest for aerospace applications. The subject epoxides of the greatest interest are 1,1,1-tri(glycidyloxyphenyl) methanes (as such or as oligomers, i.e. advancement products). The benzene rings may include up to two bromine or choro groups each and, when this option is exercized, the epoxides would be expected to have enhanced flame retardance. Although surprisingly flexible for resins with high heat distortion temperatures, the epoxides are not as tough (impact resistant) as is desirable for certain applications, such as carbon-reinforced composites for advanced air frames.

U.S. Pat. No. 4,550,129 discloses compositions of tri(glycidyloxyphenyl) methanes with a toughnessimparting resin which is a polybrominated epoxide suoh as the diglycidyl ether of tetrabromobisphenol A. These compositions have improved flame retardancy but the carbon-bromine bonds tend to be cleaved at elevated service temperatures.

High moisture resistance is critical to the retention of physical properties in the resinous components in composite structures employed in high performance aircraft. It is known that fluorocarbons of high fluorine contents are generally hydrophobic.

Tris(pentafluorophenyl)methane (m.r. 158°–159° C.) has been known since it was described in 1967 by R. Filler et al. in *J. Am. Chem. Soc.*, 89, p. 1026. Hexafluoropropylene oxide has been known since at least as early as 1952, when its preparation by electrochemical oxidation of epichlorohydridin was disclosed in British Patent No. 672,720 by E. Kauk and J. Simons. However, it has not been proposed to prepare fluorinated triphenyl methanes substituted with fluorinated (or unfluorinated) glycidyl or glycidyloxy groups. In fact, to the best of the present inventors' knowledge, incorporation of fluorine in triphenylmethane-based tris-epoxides has not even been contemplated.

OBJECTS OF THE INVENTION

The primary object of the present invention is to improve the flame and moisture resistances of cured triphenylmethane-based triepoxides (and the oligomeric reaction products thereof with various polyfunctional phenols tri(hydroxyphenyl)methanes, most notably).

A corollary object is to increase the chemical and thermal stability of the triphenylmethane-based triepoxides.

An additional object is to provide, as a new composition of matter, highly fluorinated, glycidyl, and glycidyloxy derivatives of triphenylmethane.

A further object is to provide a form of triphenylmethane based epoxide which can be toughened by admixture with fluoroelastomers (which can be cured by agents which will also cure the tris-epoxide).

Another object is to utilize novel intermediates and processes for the preparation of the epoxides of the foregoing type.

Still other objects will be made apparent to those knowledgeable in the art by the following specifications and claims.

SUMMARY OF THE INVENTION

In a compositional aspect, the present invention may be defined as the group of compounds represented by the following formula

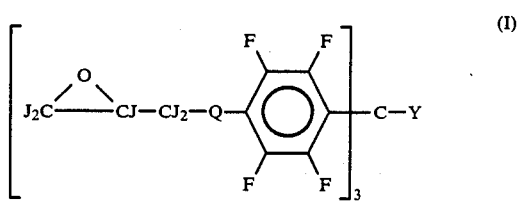

wherein
J is H or F, the same in each occurrence;
—Q— is a valence bond or —O—, the same in each occurrence; and
Y=H or F, independently.

The novel compounds represented by the following formulas (II and III) have utility as intermediates for preparation of the compounds of formula I (and constitute a separate invention not claimed in the present application):

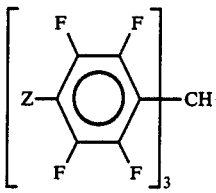

(II) Z = MO, hal.Mg, or Ag
(III) Z = J$_2$C = C—CJ$_2$—Q— wherein
M=Cs, K, Na, or Li; and
hal=Br or I.

The present invention also embraces the method of preparing a compound of formula I which comprises carrying out the following steps:

first, reacting an allylic halide of the formula CJ$_2$=CJ-CJ$_2$X, X being F, Cl, Br, or I, with a compound of formula II, thereby forming a compound of formula III;

then, if Y in said compound of formula I is to be F, converting the —CH group in the compound of formula III to a —CF group; or if Y is to be H, proceeding directly to the following step;

and finally, converting the J$_2$C=CJ-CJ$_2$— groups in the -cy-containing compound of group III to

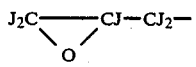

groups.

It should be noted that reaction of the H and Q trisphenol

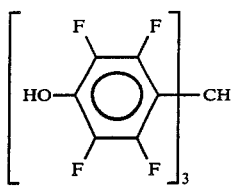

(IV)

with the allylic halide in the presence of only a catalytic amount of a base (MOH), followed by dehydrohalogenation of the initial reaction product with more base, is considered here as equivalent to reacting the allylic compound with a preformed compound of formula II in which Z=MO.

It should also be noted that when J is to be H and Q is to be O in a tris-epoxide of formula I, the tris-epoxide may be prepared simply by reaction of the corresponding trisphenol of formula IV with epichlorohydrin in essentially the manner disclosed in U.S. Pat. No. 4,394,496 for the preparation of 1,1,1-tris(glycidyloxyphenyl)methane. See Example J herein. (This process invention is not claimed in this patent.)

DETAILED DESCRIPTION

Starting and Intermediate Materials

Tris(pentafluorophenyl)methane, m.r. 158°–159.5° (from MeOH), can be obtained in 91% yield by the reaction of pentafluorobenzene with chloroform in the presence of $AlCl_3$, in a sealed reaction vessel for 4–5 hours at 150° C., according to Beckert et al., *J. Org. Chem.*, 32, 582 (1967). NMR data given by Filler et al., Communications to the Editor, *J. Am. Chem. Soc.* 189:41, February 15, 1967, wherein the subject compound is reported to have been recovered from solution in $H_2SO_4$ by dilution with water and extraction with $CCl_4$.

Perfluoroallyl chloride ($F_2C=CF-CF_2Cl$; b.p. 7.5° C.) is an intermediate employed in the process of U.S. Pat. No. 3,047,640 (1962) for the manufacture of hexafluoropropene and can also be converted to perfluoroallyl iodide or perfluoroallyl bromide) by reaction with Na I (or K Br) in acetone for 10 days at 20° C. See Miller et al., *J. Amer. Chem. Soc.*, 79, 4164 (1957).

Tris(tetrafluoro-4-hydroxyphenyl)methane (compound IV; "the trisphenol") is judged to be readily preparable by either of the following two routes.

Route 1

Tetrafluoro-p-hydroxybenzaldehyde (a) is made by the careful catalytic reduction of tetrafluoro-p-hydroxybenzoyl chloride with hydrogen (the Rosenmund method). The chloride is readily prepared from the corresponding acid (known) with thionyl chloride. See Wagner & Zook; *Synthetic Organic Chemistry*, Wiley, N.Y., 1953, pp. 291-2 and 546.

2,3,5,6-Tetrafluorophenol (also known) is condensed with the preceding aldehyde (a) by bubbling anhydrous HCl into a mixture of the aldehyde with an excess of the phenol and such amount of a solvent ("diglyme", the dimethyl ether of diethylene glycol, for example) as is required to make the mixture a liquid at 40° C. The mixture is warmed in a water bath to maintain it at about the latter temperature while the reaction is continued for at least ½ hour. The reaction product (b), tris(tetrafluoro-p-hydroxyphenyl)methane, is recovered by cooling the mixture as may be necessary to ensure precipitation of at least a substantial proportion of the tris compound, filtering and recrystallizing the filtrand from a solvent such as methanol or methylethylketone.

Route 2

Tris(pentafluorophenyl)methane is converted to the trisphenol by reacting it with KOH in t-butanol for about one hour at reflux. The reaction mixture is cooled to room temperature, neutralized with HCl, and filtered (to remove potassium halides). The filtrate may be utilized directly as a solution of the trisphenol or may be concentrated by boiling off t-butanol, and then chilled to precipitate the trisphenol, which is recovered by filtration.

Alkali metal salts of the latter trisphenol may be prepared by dissolving the trisphenol in an anhydrous solvent, MeOH, dioxane or glyme, for example, and adding three equivalents of a corresponding alkali metal alkoxide ($NaOCH_3$, for example) portionwise with cooling and stirring under dry $N_2$. The resulting reaction mixture may be employed per se or the tri alkali metal salt isolated by conventional work up methods.

Compounds of Formula II in Which Z is BrMg, IMg, or Ag

The compound [Br—Mg—$C_6F_4$—$]_3$CH is judged to be preparable (without special precautions) from tri(pentafluorophenyl)methane in at least one of the following ways:

a. reaction with six equivalents of ethyl magnesium bromide in the presence of $CoCl_2$ (or other transition metal halides) in THF (tetrahydrofuran) at 10°–0° C. for from one to several hours.

b. reaction with Mg° and at least three equivalents of $C_2H_5Br$ or $(CH_2Br)_2$ in THF at 0° C.

The compound [I—Mg—$C_6F_4$—$]_3$CH is judged to be preparable by the reaction of [Br—Mg—$C_6F_4$—$]_3$CH with 1-chloro-1,1,2-trifluoro-2-iodoethane in diethyl ether at reflux for three hours.

The compound of formula II in which Z is Ag is judged to be preparable by first reacting [Br—Mg—$C_6$-$F_4$—$]_3$CH with bromine to form tris(tetrafluoro-4-bromophenyl)methane and then reacting the latter compound with

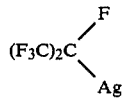

in the manner described for the preparation of $C_6F_5Ag$ (and

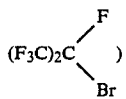

)

from $C_6F_5Br$ by Sun & Miller, *J. Amer. Chem. Soc.*, 92, 6985. (1970).

Media judged exemplary of those suitable for the reactions involved in the multi-step process of the invention as outlined above are exemplified by N-methyl pyrollidone; diethyl ether; dioxane; THF; glycol- and polyglycol- mono- and diethers; perfluorinated aliphatic and cycloaliphatic hydrocarbons; DMF (dimethyl formamide); $CH_2Cl_2$; $CHCl_3$; $CCl_4$; lower ketones, such as acetone and methyl ethyl ketone; dimethyl sulfoxide; acetonitrile; lower alcohols; and fluoroalcohols. Also believed suitable are perfluorinated acyclic and cyclic ethers, perfluoro THF and perfluoro-1,4-dioxane, for example. (Caution: Fluoroalcohols, particularly 2-fluoroethanol, are highly toxic.)

Reactions of Formula II Compounds With Perfluoroallyl Halides ($F_2C=CF-CF_2X$)

In general, it is preferred that X be Cl and, except when X is Br or I, to carry out the reactions in a closed vessel capable of withstanding the vapor pressure of the perfluoroallyl halide at the highest contemplated reaction temperature.

The subject reactions are represented by the following equations.

When J is F

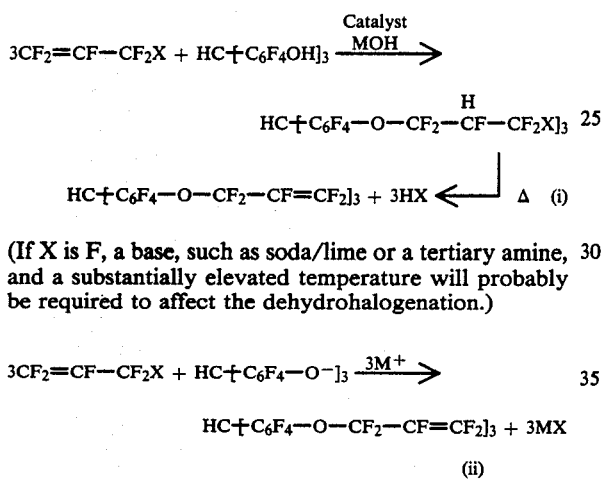

(If X is F, a base, such as soda/lime or a tertiary amine, and a substantially elevated temperature will probably be required to affect the dehydrohalogenation.)

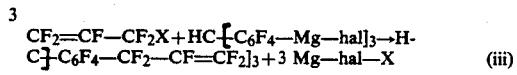

$$HC+C_6F_4-O-CF_2-CF=CF_2]_3 + 3MX$$

(ii)

MX should be more readily split out when X is Br or I.

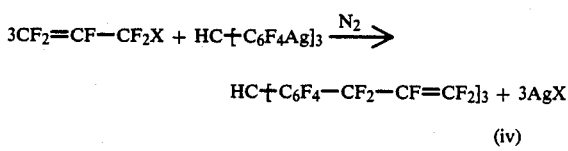

hal preferably is Br

X preferably is not F $$3CF_2=CF-CF_2X + HC+C_6F_4Ag]_3 \xrightarrow{N_2}$$

$$HC+C_6F_4-CF_2-CF=CF_2]_3 + 3AgX$$

(iv)

X preferably is not F.

Although the present invention is not posited on a correct understanding of the reaction mechanisms involved, it is believed that at least reactions i–iii involve nucleophilic attack on the orginal $CF_2$ group in the perfluoroallyl halide and that an allylic shift then occurs in reactions ii and iii. In the case of reaction iv, direct attack by silver on X is believed to occur

When J is H

Allyl halides ($CH_2=CH-CH_2X$) are considered to behave like the combination of a resonance-stabilized carbonium ion and an $X^-$ anion, to an extent dependent on the ionic character of the carbon/halogen bond. Thus, the subject reactions, when J is H, are all believed to be $SN_1$ reactions involving an attack on the formula II reactant by the allyl carbonium ion. The reactions can be represented by the following equation.

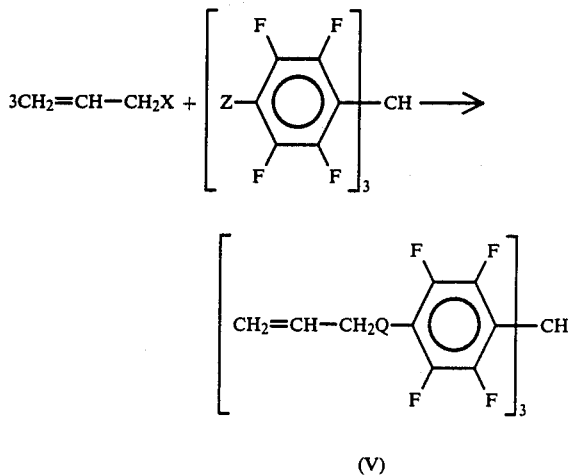

(V)

When:
Z=MO, Q=—O—, and 3 molecules of MX are formed;
Z=hal.Mg or Ag, Q is a valence bond, and 3 molecules of hal.MgX or AgX are formed.

Conversion of $\diagdown\!\!\!\!\overset{\diagup}{C}H$ in Formula III Compounds to $\diagdown\!\!\!\!\overset{\diagup}{C}F$

When J is F

It is judged that the subject conversion can be achieved by using any of the several fluorinating agents which have not been shown to form irreversible adducts with $F_2C=CF$ groups and have been used to make trityl fluoride, (phenyl)$_3$CF. The preferred such reagent is $NO^+BF_4^-$/pyridine polyhydrogen fluoride: Olah et al., J. Org. Chem, 48, 3356-8, (1983). Other such reagents are $NH_4F$, (German patent No. 2,105,907, 1971); $(C_4H_9)_4NF$, J. Org. Chem, 49, 3216, (1984); and $CH_3COF$, J. Amer. Chem. Soc., 46, 1515, (1924). $F_3COF$, which does not add to aromatic C=C groups, may also be suitable.

When J is H

In this case, the Olah reagent is highly preferred, since it is specific for tertiary CH groups. However, when it is judged that replacement with F of one or more of the hydrogens in the allyl groups of formula III will not interfere with subsequent "epoxidation" of the double bonds in these groups, other of the above named fluorinating agents may be suitable.

"Epoxidation" of the Allylic Double Bonds

When J is H

Conventional methods of converting allyl- or allyloxyphenyl groups to glycidyl or glycidyloxy phenyl groups may be employed. Such methods are based generally on those described for epoxidation of olefins in chapter 7 of Wagner & Zook, *Synthetic Organic Chemistry*, Wiley & Sons, N.Y., 1953. One such method is treatment of the olefin with a peracid in chloroform solution at 0°–5° C. (in the manner disclosed in U.S. Pat. No. 2,965,607 for direct epoxidation of the allyl groups in mono- and diallyl -2,3-epoxypropyl benzenes). Alternatively, a hypohalous acid may be formed in situ and added to the double bonds to produce a tris-halohydrin which may then be dehydrohalogenated with a base.

Another oxidation method is to treat the triallyl compound with $H_2O_2$ in an alkaline medium, such as KOH in n-butanol.

When J is F

It is judged that compounds of the following formula

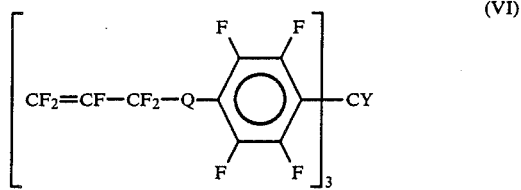

(VI)

can be converted to the corresponding epoxides by modifications of some of the methods which have been shown suitable for converting perfluoropropylene (b.p. - 29° C.) to perfluoropropylene oxide. The preferred method is oxidation with 30% aqueous $H_2O_2$NaOH at 20° C. in a reaction medium such as n-butanol or a fluoroalcohol (a modification of the method summarized in equation 485, page 203 of Hudlicky, *Chemistry of Organic Fluorine Compounds, A Laboratory Manual;* referencing British Patent No. 904,877 (1962)).

An alternative method is photolytic oxidation with $O_2$ in perfluoroheptane (a good solvent for oxygen; b.p. ~80° C.) at room temperature. Preferably, the latter oxidation is carried out in a multi-capillary photoreactor of the type disclosed in U.S. Pat. No. 4,456,512. It is believed that substantial oxirane/oxirane interaction of the type which results in uv catalyzed polymerization of perfluropropylene oxide will not occur, because the desired tris-epoxides do not include the strongly election withdrawing —$CF_3$ group present in perfluoropropylene oxide.

For the same reason, it is anticipated that hydrolysis of the tris-epoxides will be of less concern than in the case of perfluoropropylene oxide. However, it is considered advisable to minimize access of moisture to the tris-epoxides, once formed, even though prepared in (basic) aqueous media. Again, for the same reason, perfluoroglycidyl groups in epoxides of the invention are expected to exhibit substantially higher thermal stabilities than does perfluoropropylene oxide.

Methods of Isolating and/or Identifying the Compounds of Formulas I and III

In this regard, reference may be had to Chapter 8 of Hudlicky (loc. cit.), pages 558–594. In addition, it may be noted that perfluorolefin epoxides (such as perfluoropropylene oxide) exhibit a characteristic infrared absorption bond at 6.4–7.2 microns (according to British Patent No. 904,877). It should be kept in mind that perfluorocarbons in general, particularly perfluoroaromatics, tend to form solid complexes with some solvents and tend to associate most strongly with protic (H-binding) solvents.

The conventional method of EEW (epoxide equivalent weight) determination is believed to be suitable for characterization of the tris-epoxides of the present invention.

The intermediate compounds of the formula $(CJ_2=CJ—CJ_2—Q—C_6F_4)_3CY$ each containing three carbon-to-carbon double bonds which will take up one molecule of bromine each and thus can be titrated colorimetrically. That is, the grams of $Br_2$ (mol. wt. - 159.84) which can be taken up by one mole (M grams) of the triallyl compound is $3 \times 159.84$; or the grams of a triallyl compound of molecular weight M required to consume one gram of bromine is $M/(3 \times 159.84)$; or the theoretical number of grams of an ostensible triallyl compound of the above formula required to consume one gram of bromine is equal to $M/479.52$. The actual bromine uptake is determined in the classical manner. A known weight ($W_c$) of the compound is dissolved in $CCl_4$, conveniently in an Elenmeyer flask with magnetic stirring, and a $Br_2$ in $CCl_4$ solution of known molality is added from a pipette dropwise with smooth stirring until the last drop added has not decolorized after ten minutes. $W_c$ is divided by $W_{Br}$, the weight of the bromine in the volume of solution added. (The temperature of the reaction mixture should be kept at about 25° C. or lower to prevent substantial replacement of H by Br. When J in the compound is F, irradiation with ultraviolet light may be employed to speed up the addition of the bromine to the double bonds.)

Curing of the Epoxides of the Invention

A desideratum in all procedures for curing the subject epoxides is to minimize losses of fluorine (as HF or otherwise). Accordingly, catalytic, effectively nonprotic curing agents are preferred for curing of formula I epoxides and avoidance of high temperatures in the first stage of curing of all of the subject epoxides is advisable. It must be kept in mind that at least one of the four fluorines on each of the three benzene rings may be replaceable by strong nucleophiles at elevated temperatures.

The epoxides derived from the tri-allyl compounds of the foregoing formula V may be cured with either catalytic or co-reactive curing agents. Representative of suitable catalytic agents are $BF_3$.MEA (Boron trifluoride monoethylamine), N-aminoethyl piperazine and "EMI-24", a substituted imidazole. Representative co-reactive agents are meta-phenylene diamine (MPDA), methylene dianiline (MDA), diaminodiphenyl sulfone (DDS or DADS), phthalic anhydride (PA), hexahydrophthalic anhydride (HHPA), maleic anhydride (MA), nadic methyl anhydride (NMA), bisphenols and polyamides (such as dicyandiamide.) The most preferred agents are MDA and DADS. A cure schedule of two hours at 60°–100° C. and 5–18 hours at 150°–180° is recommended. See U.S. Pat. No. 4,394,496.

The epoxides derived from the tri(perfluoroallyl) compounds of the foregoing formula VI are expected, on average, to react with curing agents in a manner more similar to that of perfluoropropylene oxide than to the epoxides of the '496 patent. Consequently, catalytic curing agents, particularly those of the type which catalyze oligomerization of perfluoropropylene oxide are preferred. The latter type of catalytic agents include alkali metal fluorides (CsF in particular), tertiary amines, amine oxides, and quaternary alkyl/aryl ammonium, phosphonium, or arsonium salts.

Co-reactive cross-linkers believed to be suitable are quaternary ammonium salts of bisphenols such as, for example, hydroquinone or tetrafluorohydroquinone. The latter salts may be formed in situ from a metal salt of the bisphenol and a quaternary halide.

The combination of the dipotassium salt of hydroquinone and benzyltriphenyl phosphonium chloride has been used to provide a nucleophilic cross-linker for vinylidene fluoride/hexafluoropropylene copolymers and for tetrafluoroethylene/perfluoroalkyl vinyl ether copolymers.

In view of the known behavior of diethylamine with perfluoropropylene oxide, piperazine is also believed to be suitable as a co-reactive cross-linker for the epoxides of the present invention. When the epoxide is derived from a tri(perluoroallyl) compound of formula VI, it may be desirable to include MgO in the formulation.

The preferred formulation solvents for the curing reaction of all formula I epoxides are relatively low boiling ethers such as THF, glyme, perfluoro THF, and perfluorodioxane.

The epoxides derived from the precursors of formula VI are expected to be more reactive than those derived from the precursors of formula V and accordingly to require shorter cure times and/or lower temperatures than are employed in the cure schedules set out above.

EXAMPLES

The following examples (prophetic) are for purposes of illustration and are not to be construed as limiting the present invention in a manner inconsistent with the claims in this patent.

Examples A-I are of the preparation of intermediates not claimed in the present application. Examples 1-3 are of preparations of the compounds of the present invention (formula I). Examples B, C, E, F(2), and G are examples of the first step in the process claimed in this patent. Examples H and I are examples of the intermediate step required when Y is to be F in the compound of formula I. Examples 1-3 are examples of the final step in the process.

A. Preparation of HC($-C_6F_4MgBr$)$_3$ solution by "entrainment reaction" of EtBr with Mg° and HC($C_6F_5$)$_3$ in THF A few ml of a solution of three molecular proportions of EtBr in THF* is added at once with stirring (under dry $N_2$) to a solution of one molecular proportion of HC($C_6F_5$)$_3$ in THF* and 7.5 atomic proportions of Grignard grade metallic magnesium turnings, thereby initiating the reaction. Thereafter, the rest of the EtBr solution is added dropwise and an ice water bath is used to moderate the reaction. When the addition is complete (should require at least 45 minutes), the cooling bath is removed and the reaction mixture allowed to stir for an additional period of about 45 minutes.
* Freshly distilled from calcium hydride.

The reaction mixture is transferred (still under dry $N_2$) to a rotary vacuum distillation apparatus and the unconverted EtBr (and some of the THF) removed under a sufficiently reduced pressure so that the "kettle" temperature does not exceed about 30° C. The residual solution (which includes uncoverted HC($C_6F_5$)$_3$ is chilled in the kettle under reduced pressure. The distillation system is filled with dry nitrogen and the kettle is removed and immediately stoppered. If not used shortly thereafter, it should be stored in a freezer for future** use.
** Since about 15 mole percent of the HC($C_6F_5$)$_3$ is expected to remain unconverted and to tend to itself react with the Grignard compound, the solution should be used within about 24 hours.

B. Preparation of ($H_2C=CH-Ch_2-C_6F_4$)$_3$CH from the Grignard solution of Example A and allyl chloride The Grignard solution is transferred (under dry $N_2$) to a suitable reaction assembly, warmed to about 30° C. and stirred, if necessary, until homogeneous. Four molecular proportions of purified allyl chloride are added from a pressure-equalized dropping funnel at a rate such that the resulting reaction mixture can be kept at about 25°-30° with water bath cooling as necessary. The mixture is allowed to stir at room temperature for about an hour, brought to a boil, and held at reflux (with stirring) for at least an hour. It is subsequently cooled, filtered to remove MgBrCl and stripped of allyl chloride and THF at ambient pressure, with stirring. When about half of the THF has been removed, addition of ethanol is commenced and stripping is continued until the boiling point of the solution approximates that of ethanol. The solution is cooled and the triallyl compound separated (from unconverted HC($-C_6F_5$)$_3$ carried over from the preparation of the Grignard) by fractional crystallization and dried, first in a vacuum oven at 60° C. and then in a dessicator over $P_4O_{10}$. The dried product is recrystallized; separate samples are titrated with bromine and subected to elemental analysis. The grams of product required per gram of $Br_2$ is about 1.2 (vs. 580.41/479.52=1.21 theor.) and the chemical composition corresponds to the emperical formula ($C_{28}H_{16}F_{12}$) of the title compound.

C. Preparation of ($F_2C=CF-CF_2-C_6F_4$)$_3$CH from perfluoroallyl bromide and (BrMg—$C_6F_4$)$_3$CH The Grignard reagent is provided as a solution of the type prepared in Example A. The procedure followed is that of Example B above, except that more ethanol may have to be boiled off (to ensure complete removal of the unconverted perfluoroallyl bromide, which should boil at about 70° C.) before stripping is terminated. (The salt filtered out, of course, is $MgBr_2$, not MgBrCl.) The concentrated solution is chilled and a crude product obtained by fractional crystallization. The latter product is recrystallized. Separate samples are titrated with bromine and subjected to elemental analysis. The grams of sample per gram of bromine is about 1.8 (vs. 850.2/479.52=1.77 theor.) and the chemical composition found corresponds to the emperical formula ($C_{28}HF_{27}$) of the title compound.

D. Preparation of HC($C_6F_4Ag$)$_3$, from (Br—$C_6F_4$)$_3$CH, AgF, and $CF_2=CF-CF_3$ (the latter two reacting in situ to form $CF_3-CFAg-CF_3$)

The (Br-$C_6F_4$)$_3$CH is prepared from the corresponding Grignard (Example B) by transferring the THF solution (under dry $N_2$) to a pressurizeable, glass-lined reactor, such as a Pfaudler kettle, warmed to about 25° C. and stirred, if necessary, until homogeneous. 3.1 molecular proportions of bromine are added from a pressure-equalized dropping funnel, with stirring, at a rate such that the reaction mixture can be maintained at about 25°-30° C. with water cooling as necessary. The mixture is allowed to stir at room temperature for about an hour, heated and held at reflux with stirring for about an hour. It is then cooled, filtered to remove $MgBr_2$, returned to the kettle, and stripped of THF at ambient pressure. When about half the THF has been removed, addition of acetonitrile (reagent grade) is commenced and stripping is continued until the boiling boint of the reaction mixture rises to about 80° C. The resulting solution of (BrC₆F₄)₃CH and the unconverted (C₆F₅)₃CH carried over from the Grignard preparation) is cooled to about 25° C. and then, with stirring, a dispersion of three molecular proportions of AgF in a minimum of CH₃CN is added and subsurface introduction of gaseous perfluoropyropylene from a cylinder (on a scale) at a low rate is begun. The otherwise closed reaction system includes a dry nitrogen pad and is connected to an open ended, tapered dip tube inserted to a depth of several inches in a silicone oil. An anti suckback arrangement is included. The perfluoropylene in-flow is controlled so that the meniscus in the dip tube remains about an inch from the tube end, the reaction mixture being cooled as necessary to maintain it at about 25° C. The in-flow is continued until the uptake rate is negligible. The mixture is then filtered, if necessary, and may be utilized as a solution of the title compound. At least a portion of it is concentrated under reduced pressure. The solid obtained by chilling and filtering the concentrate is recrystallized and the resulting product found to have a composition corresponding to the minimum emperical formula (C₁₉HAg₃F₁₂) of the title compound.

E. Preparation of (F₂C=CF—CF₂—C₆F₄)₃CH by reaction of F₂C=CF—CF₂—Cl with (AgC₆F₄)₃CH To a solution in acetonitrile of one molecular proportion of the silver compound, under dry nitrogen, is added 3.1 molecular proportions of perfluoroallyl chloride, with stirring. The resulting mixture is stirred at room temperature for about 72 hours, filtered to removed AgCl and stripped under reduced pressure in a rotary apparatus. The solid residue is recrystallized and separate samples of the final product are titrated with bromine and subjected to elemental analysis. The grams of product per gram Br₂ found is about 1.8 (vs. 1.77 theor.) and the chemical composition found corresponds to the minimum emperical formula (C₂₈HF₂₇) of the title compound.

F. Preparation of HC–(–C₆F₄—O—CF₂—CF=CF₂)₃ from perfluoroallyl bromide and the tri-sodium salt of the trisphenol A solution of 3.05 molecular proportions of sodium methoxide in anhydrous methanol is added, with stirring and under dry nitrogen, to a solution of one molecular proportion of the trisphenol, (HOC₆F₄)₃CH, in anhydrous methanol. The rate of addition is controlled as necessary to keep the reaction mixture from exceeding 30° C. After addition is complete, the mixture is stirred for about an hour. To it, 3.1 molecular proportions of the perfluoroallyl bromide are then added as a thin stream, the reaction mixture being cooled as necessary to hold it at a temperature of 25°-40° C. When the addition is complete, the reaction mixture is stirred at room temperature for about an hour and then filtered to remove NaBr. The filtrate is stripped under reduced pressure in a rotary apparatus. The solid residue is recrystallized and separate samples of the final product are titrated with bromine and subjected to elemental analysis. The grams of product per gram of Br₂ found is about 1.9 (vs. 898.2/479.52=1.87 theor.) and the chemical composition found corresponds to the emperical formula (C₂₈HF₂₇O₃) of the title compound.

G. In essentially the same manner as in Example F, (CH₂=CH—CH₂—O—C₆F₄)₃CH is prepared from allyl chloride and the tri-sodium salt of (HO—C₆F₄)₃CH.

H. Preparation of (CH₂=CH—CH₂—C₆F₄)₃CF from (CH₂=CH—CH₂—C₆F₄)₃CH

To a solution of 1.25 molecular proportions of NO⁺BF₄⁻ in 70% pyridine polyhydrogen fluoride (1.2 liters per mole NO⁺BF⁻) in a Teflon reaction vessel provided with a Teflon stirrer and immersed in an ice-/water bath is slowly added a solution of one molecular proportion of (CH₂=CH—CH₂—C₆F₄)₃CH in 500 ml of CH₂Cl₂ with continuous stirring. The resulting mixture is stirred at room temperature for several hours, poured into and stirred with ice water, and then extracted three times with a water immiscible solvent such as diethyl ether or perfluorohexane. The combined extracts are washed successively with water, aqueous NaHCO₃ and brine, then dried over anhydrous MgSO₄ and stripped under gradually reduced pressure. The residual crude product is recrystallized. Separate samples of the final product are titrated with bromine and subjected to elemental analysis. The grams of product per gram of bromine is about 1.3 (vs. 598.40/479.52=1.25 theor.) The chemical composition formed corresponds to the emperical formula (C₂₈H₁₅F₁₃) for the title

compound.

I. Each of (CH₂=CH—CH₂—O—C₆F₄)₃CF, (CF₂=CF—CF₂—C₆F₄)₃CF, and (CF₂=CF—CF₂—O—C₆F₄)₃CF are prepared by essentially the procedure of Example F from the corresponding

compound.

J. Preparation of

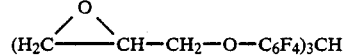

from epichlorohydrin, the corresponding trisphenol, a coupling catalyst and a base Into a flask fitted with a stirrer, thermometer, and reflux condenser is placed one molecular proportion of the trisphenol (HOC₆F₄)₃CH, 30 molecular proportions of epichlorohydrin, and one part by weight per hundred parts of the trisphenol of a commercial 60% solution of benzyltrimethyl ammonium chloride. The flask contents are heated with stirring to boiling (~119° C.), held at reflux for an hour and cooled. The flask is then placed in a 50° C. water bath and three molecular proportions of NaOH, as a three molar solution in saturated aqueous Na$_2$CO$_3$ is added. The resulting two phase mixture is stirred at 50° C. for an hour and then allowed to phase separate. The spent NaOH solution is separated. The epichlorohydrin solution is returned to the flask, heated in the 50° C. water bath, and treated again with half the orginal amount of fresh three molar NaOH in saturated Na$_2$CO$_3$ solution. The spent caustic is again separated. The organic phase is washed with dilute aqueous acetic acid, then with water until neutral to the litmus paper. The water and the unconverted epichlorohydrin are distilled off under vacuum in a rotary distillation apparatus. A portion of the resinous residue is analyzed by GPC (Gel Permeation Chromatography) and found to include some oligomeric material but to consist essentially of monomeric material. The EEW of the solid residue is determined to be within the range of 214 to about 221. The monomeric tris-epoxide (C$_{28}$H$_{16}$F$_{12}$O$_6$; EEW 212.1) is separable from the resinous residue by preparative GPC.

1. Preparation of

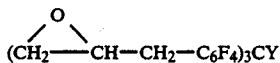

(Y=H or F) by epoxidation of (CH$_2$=CH—CH$_2$—C$_6$F$_4$)$_3$CY with peracetic acid To a solution of one gram molecular weight of the triallyl compound in CHCl$_3$ at 20°–30° C. is added 489 grams of 45% peracetic acid solution in CHCl$_3$. When the addition is complete, the resulting mixture is stirred at 30° for two hours, then for 12 hours at 27° C. The reaction mixture is extracted with water, aqueous Na$_2$CO$_3$ and water, then filtered, dried over anhydrous MgSO$_4$, and stripped under reduced pressure in a rotary apparatus. The EEW of the solid residue is determined to be within the range of from about 197 to 206, when Y is H, or from about 213 to 220 when Y is F. The residue is subjected to elemental analysis and is found to have a chemical composition corresponding to the minimum emperical formula or (C$_{28}$H$_{16}$F$_{12}$O$_3$ or C$_{28}$H$_{15}$F$_{13}$O$_3$) for the title compound (molecular weight 588.41 or 646.40 respectively).

2. Preparation of

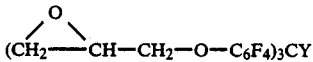

(Y=H or F) by epoxidation of (CH$_2$=CH—CH$_2$—O—C$_6$F$_4$)$_3$CY with peracetic acid Essentially the same procedure as in Example 1 is employed. When Y is H, the EEW found is within the range of from about 214 to 221 and the chemical composition found corresponds to C$_{28}$H$_{16}$F$_{12}$O$_6$ (M=636.41). When Y is F, the EEW found is within the range of from about 232 to 240 and the chemical composition found corresponds to C$_{28}$H$_{15}$F$_{13}$O$_6$ (M=694.40).

3. Preparation of

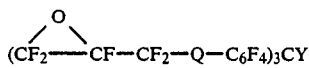

by epoxidation of (CF$_2$=CF—CF$_2$—Q—C$_6$F$_4$)$_3$CY with alkaline H$_2$O$_2$. (—Q—=—* or O and Y=H or F.)

* The symbol—represents a valence bond

To a solution of one molecular proportion of the perfluoroallyl compound in chloroform is added six molecular proportions of H$_2$O$_2$, as a 35% solution, with stirring and at room temperature. Three molecular proportions of Na$_2$CO$_3$ as a saturated aqueous solution are added with stirring. The resulting mixture is stirred overnight at room temperature and then phase separated. The organic phase is stripped in a rotary apparatus under reduced pressure and the residual crude product recrystallized. The EEW of the final product is determined and a sample of the product is subjected to elemental analysis. The chemical composition found for each of the products listed in the following table corresponds to the emperical formula given for that product. The actual and theoretical EEW's (molecular weights divided by three) are given in the table.

| Q | Y | Emperical Formula | Theoretical EEW | Range in which EEW found residues |
|---|---|---|---|---|
| — | H | C$_{28}$HF$_{27}$O$_3$ | 299.4 | 300–320 |
| — | F | C$_{28}$F$_{28}$O$_3$ | 305.4 | 306–325 |
| O | H | C$_{28}$HF$_{27}$O$_6$ | 315.4 | 316–330 |
| O | F | C$_{28}$F$_{28}$O$_6$ | 321.4 | 322–340 |

4. Properties of cured tris-epoxides of the invention

Standard (ASTM) cured test specimens are prepared from formulations of each of the epoxides of the foregoing Example 2 with each of the co-reactive curing agents MDA, MPDA, DADS, and maleic anhydride, using standard stoichiometry. The specimens are tested by ASTM methods and are found to exhibit superior moisture resistance, flame retardance, and thermal stability, and as high or higher heat distortion temperatures, as compared to otherwise identical formulations of those tris-epoxides of U.S. Pat. No. 4,394,496 which contain two chlorines on each of the benzene rings. The cured epoxides of Example 3 in which Q is a valence bond are less flexbile and would preferably be formulated with a flexibilizer, such as a fluoroelastomer.

Similarly, cured specimens are prepared from formulations of each of the epoxides of Example 3 with the following catalytic or co-reactive curing agents: BF$_3$.MEA, EMI-24, benzyltriphenyl phosphonium chloride, and tetrafluorohydroquinone. When tested, these specimens exhibit superior moisture resistance, flame retardance, and thermal stability, and as high or higher heat distortion temperatures as compared to those tris-epoxides of the '496 patent which contain two chlorines on each benzene ring.

What is claimed is:

1. The tris-epoxides represented by the formula

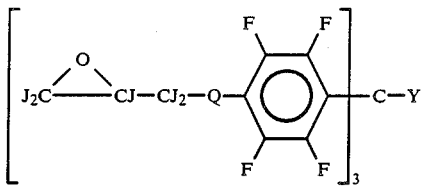  (I)

wherein
J is H or F, the same in each occurrence;
—Q— is a valence bond or —O—, the same in each occurrence; and
Y=H or F, independently.

2. The epoxides of claim 1 in which J is H.
3. The epoxides of claim 2 in which —Q— is —O—.
4. The epoxides of claim 3 in which Y is H.
5. The epoxides of claim 1 in which J is F.
6. The epoxides of claim 5 in which —Q— is —O—.
7. The epoxides of claim 6 in which Y is F.
8. The epoxides of claim 2 in which —Q— is a valence bond and Y is H.
9. The epoxides of claim 5 in which —Q— is a valence bond and Y is H.
10. The epoxides of claim 5 in which —Q— is a valence bond and Y is F.
11. The method of preparing an epoxide of the formula

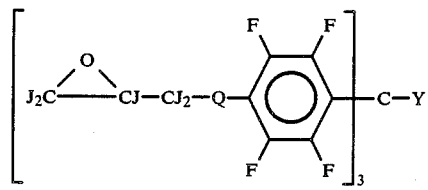  (I)

wherein
J is H or F, the same in each occurrence;
—Q— is a valence bond or —O—, the same in each occurrence; and
Y=H or F, independently,
by carrying out the following steps:
first, reacting an allylic halide of the formula $CJ_2=CJ-CJ_2X$, X being F, Cl, Br, or I, with a compound of the formula

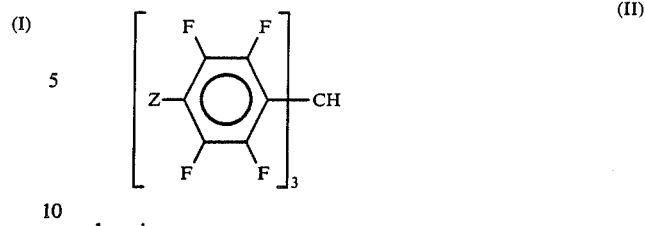  (II)

wherein
Z=MO-, hal. Mg- or Ag
M=Cs, K, Na, or Li; and
hal=Br or I.
thereby forming a compound of the formula

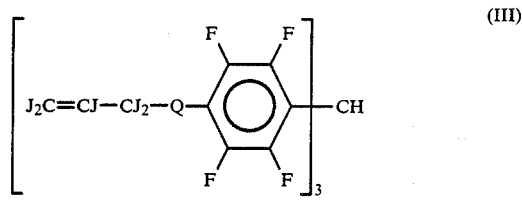  (III)

then, if Y in said epoxide formula I is to be F, converting the compound of formula III to the corresponding compound of the formula

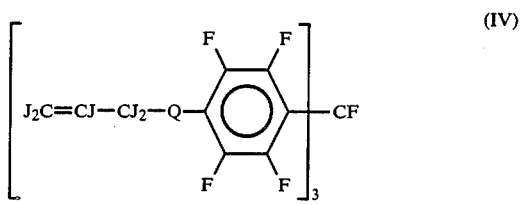  (IV)

and finally, converting the compound of formula III or IV to the compound of formula I in which Y is H or F respectively.

12. The method of claim 11 wherein —Q— is —Q—, X is Cl, and Z is NaO-.
13. The method of claim 11 wherein —Q— is a valence bond, X is Br, and Z is BrMg or Ag.
14. The method of claim 11 in which Y is F and the compound of formula III is converted to a compound of Formula IV by treatment with NO+BF-/pyridine polyhydrogen fluoride.
15. The method of claim 11 wherein J is H and the final step is accomplished by treating the compound of formula III or IV with peracetic acid.
16. The method of claim 11 wherein J is F and the final step is accomplished by treating the compound of formula III or IV with hydrogen peroxide in the presence of a base.
17. An epoxide of claim 1, cured.

* * * * *

UNITED STATES PATENT AND TRADEMARK OFFICE
CERTIFICATE OF CORRECTION

PATENT NO. : 4,717,760

DATED : January 5, 1988

INVENTOR(S) : Theodore L. Parker; Robert R. Stringham

It is certified that error appears in the above-identified patent and that said Letters Patent is hereby corrected as shown below:

Col. 1, lines 30 and 31, delete "toughnessimparting" and insert -- toughness-imparting --;

Col. 1, line 31, "such" has been misspelled;

Col. 3, line 1, delete "H and Q";

Col. 5, lines 43 and 44, formula should read as follows:

(III) ;

Col. 7, line 31, delete "H2O2NaOH" and insert -- $H_2O_2$/NaOH --;

Col. 7, line 44, "perfluoropropylene" has been misspelled;

Col. 13, line 47, after "formula" delete "or";

Col. 16, line 26, after "epoxide" insert -- of --;

Col. 16, line 41, delete "-Q- is -Q-" and insert -- -Q- is -O- --.

Signed and Sealed this

Twenty-fourth Day of January, 1989

Attest:

DONALD J. QUIGG

*Attesting Officer*  *Commissioner of Patents and Trademarks*